United States Patent
Negishi (10) Patent No.: US 7,566,301 B2
(45) Date of Patent: Jul. 28, 2009

(54) ELECTRONIC ENDOSCOPE APPARATUS (75) Inventor: Kiyoshi Negishi, Saitama (JP)

(73) Assignee: HOYA Corporation, Tokyo (JP)

( * ) Notice: Subject to any disclaimer, the term of this patent is extended or adjusted under 35 U.S.C. 154(b) by 318 days.

(21) Appl. No.: 11/428,752

(22) Filed: Jul. 5, 2006

(65) Prior Publication Data
US 2007/0010713 A1    Jan. 11, 2007

(30) Foreign Application Priority Data
Jul. 6, 2005    (JP)    ............... 2005-197301

(51) Int. Cl.
*A61B 1/06*    (2006.01)

(52) U.S. Cl. .............. 600/178; 600/118; 600/132

(58) Field of Classification Search .............. 600/109, 600/112, 118, 132, 136, 160, 172, 178; 362/10, 362/572, 574; 385/117, 118
See application file for complete search history.

(56) References Cited

U.S. PATENT DOCUMENTS

| | | | | |
|---|---|---|---|---|
| 4,407,272 | A | * | 10/1983 | Yamaguchi .............. 600/109 |
| 6,110,107 | A | * | 8/2000 | Bellahsene et al. .......... 600/182 |
| 6,322,497 | B1 | | 11/2001 | Takahashi |
| 7,018,331 | B2 | * | 3/2006 | Chang et al. .............. 600/182 |

FOREIGN PATENT DOCUMENTS

| | | |
|---|---|---|
| JP | 2003-305008 | 10/2003 |
| JP | 2006-006803 | 1/2006 |
| JP | 2006-006832 | 1/2006 |
| JP | 2006-051151 | 2/2006 |
| JP | 2006-136519 | 6/2006 |
| JP | 2006-149933 | 6/2006 |
| JP | 2006-149939 | 6/2006 |

OTHER PUBLICATIONS

U.S. Appl. No. 11/428,596 to Negishi, which was filed on Jul. 5, 2006.
U.S. Appl. No. 11/428,673 to Negishi, which was filed on Jul. 5, 2006.
English language Abstract of JP 2003-305008.
English language Abstract of JP 2006-6803.
English language Abstract of JP 2006-6832.
English language Abstract of JP 2006-051151.

* cited by examiner

*Primary Examiner*—John P Leubecker
*Assistant Examiner*—Samuel Candler
(74) *Attorney, Agent, or Firm*—Greenblum & Bernstein, P.L.C.

(57) ABSTRACT

An electronic endoscope apparatus includes an endoscope light source unit for making illumination light from a light source incident on an incident end face of a light guide of a scope which is detachably connected to a processor, the endoscope light source unit being built in the processor; a main switch for turning ON the processor; a scope lock lever for activating a lock mechanism for preventing the connected scope from coming off the processor; a light source switch for turning ON and OFF the endoscope light source unit; and a controller for turning ON the endoscope light source unit when one of the main switch and the scope lock lever is operated before the light source switch is operated while the endoscope light source unit is OFF.

7 Claims, 6 Drawing Sheets

ELECTRONIC ENDOSCOPE APPARATUS

BACKGROUND OF THE INVENTION

1. Field of the Invention

The present invention relates to an electronic endoscope apparatus having a built-in endoscope light source unit that is suitable for an endoscope, or an electronic endoscope, etc.

2. Description of the Related Art

Recent electronic endoscope systems have a processor with a built-in light source unit, to which an electronic scope having an electronic camera mounted on the distal end thereof or a fiber scope for conducting observation only through optical members is connected for use. In particular, electronic scopes have been provided for use with a wide variety of thicknesses and functions suited to different locations of observation. Processors connectable with various types of electronic scopes and fiber scopes must also have light source units that are compatible with such various electronic scopes and fiber scopes. For this reason, conventional light source units have been constructed so as to supply necessary amounts of light to electronic scopes that require maximum light intensities.

Such light source units are configured such that illumination light emitted from a high-intensity lamp is condensed by a condenser lens and made incident on the incident end face of a scope light guide, typically an optical fiber bundle. Since the necessary amount of illumination light varies with the type of electronic scope and with the observation location, the light source units are equipped with an aperture device for adjusting the amount of light mechanically. Among known aperture devices is one that includes a diaphragm which is composed of a partly-notched portion and an arm portion integrated with the partly-notched portion, having such a size that all the light from a light source lamp can be blocked; and a motor mechanically connected to an end of the arm portion. The motor is rotated to turn the diaphragm about the top of the arm portion, thereby adjusting the illumination intensity (see Japanese Patent Laid-Open Publication No. 2003-305008). Moreover, a light shielding plate may be provided with a plurality of aperture openings having different opening ratios or transmittances, and which regulates the amount of light incident on the incident end face of a light guide by putting one of the aperture openings selectively between a light source unit and the incident end face (i.e., into the illumination optical path) of the scope light guide.

Conventional electronic endoscope apparatuses have a main switch for turning ON a processor power supply and a light source switch for turning ON a light source unit separately. Typically, when the main switch is turned ON, an imaging circuit is activated to drive the electronic camera of an electronic scope connected thereto, so that captured images are displayed on a monitor display.

However, when the main switch alone is turned ON, it is impossible to insert the electronic scope into a body cavity or the like since the illumination unit is not yet turned ON. Consequently, it has been necessary to make troublesome operations of turning ON the main switch as well as turning ON the light source switch.

SUMMARY OF THE INVENTION

The present invention has been achieved in view of the foregoing conventional technology. The present invention provides an electronic endoscope apparatus which makes it possible to turn ON an endoscope light source unit without requiring an exclusive switch member to be operated.

According to an aspect of the present invention, an electronic endoscope apparatus is provided, including an endoscope light source unit for making illumination light from a light source incident on an incident end face of a light guide of a scope which is detachably connected to a processor, the endoscope light source unit being built in the processor; a main switch for turning ON the processor; a scope lock lever for activating a lock mechanism for preventing the connected scope from coming off the processor; a light source switch for turning ON and OFF the endoscope light source unit; and a controller for turning ON the endoscope light source unit when the main switch or the scope lock lever is operated before the light source switch is operated while the endoscope light source unit is OFF.

It is desirable for the processor to include a scope lock switch for detecting whether the scope lock lever is in a locked state. The controller turns ON the endoscope light source unit when the scope lock switch detects the locked state.

It is desirable for the controller to select one of the main switch, the scope lock switch, and the light source switch as a condition for turning ON the endoscope light source unit, so that the controller turns ON the endoscope light source unit when the one of the main switch, the scope lock switch, and the light source switch is turned ON.

It is desirable for the controller to select the main switch as a condition for turning ON the endoscope light source unit, so that the controller turns ON the endoscope light when the main switch is turned ON.

It is desirable for the controller to select the scope lock switch as a condition for turning ON the endoscope light source unit, so that the controller turns ON the endoscope light when scope lock switch is operated in a locked state.

While the scope lock switch is not in the locked state, it is desirable for the controller to turn ON the endoscope light when the light source switch is turned ON.

It is desirable for the controller to turn OFF the endoscope light source unit when one of the main switch and the light source switch is turned OFF.

The present disclosure relates to subject matter contained in Japanese Patent Application No.2005-197301 (filed on Jul.6, 2005) which is expressly incorporated herein in its entirety.

DETAILED DESCRIPTION OF THE PREFERRED EMBODIMENT

Figure 1:
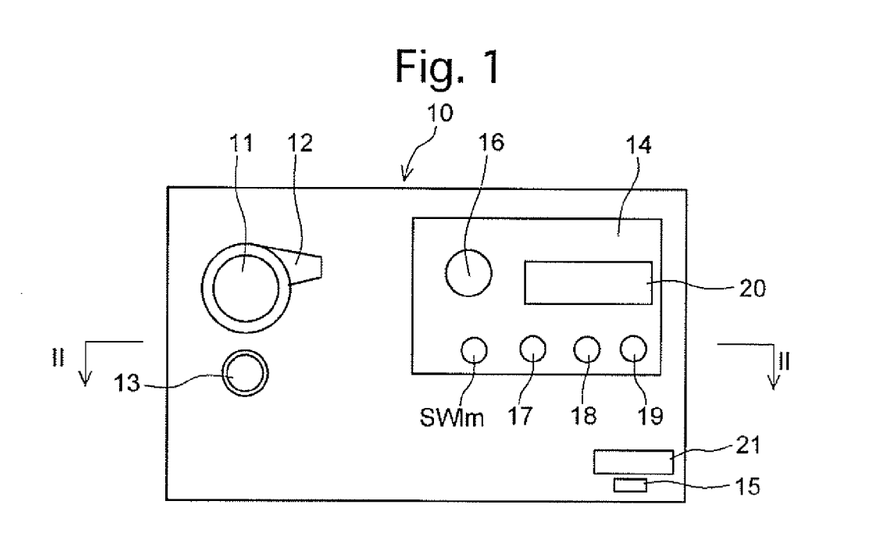
FIG. 1 is a front view showing an overview of an embodiment of a processor to which an endoscope light source unit according to the present invention is applied.
Figure 2:
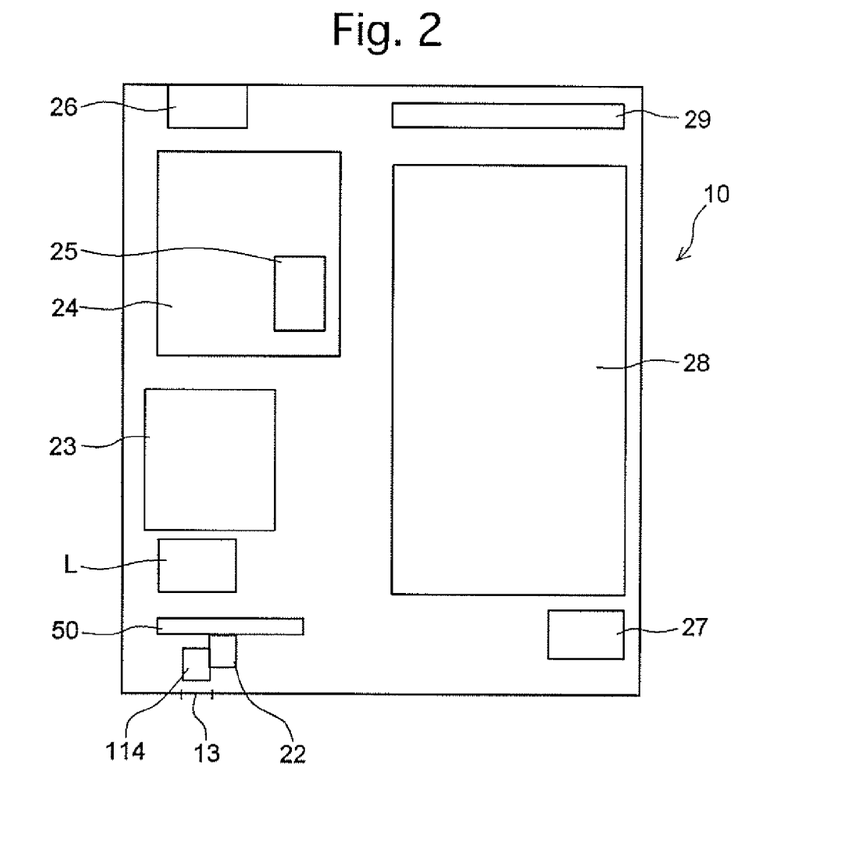
FIG. 2 is an abbreviated cross sectional view taken along the II-II line of FIG. 1, showing essential components of the processor.

Embodiments of the invention will be described with reference to the accompanying drawings. FIG. 1 is a front view of a processor (endoscope light source unit) 10 that contains a power supply unit to which the present invention is applied. Fig. 2 is an abbreviated cross sectional view taken along the II-II line of in FIG. 1, showing essential components of the processor 10.

The processor 10 is provided on the front thereof (as viewed in FIG. 1) with a scope socket 11 into which a connector 104 of an electronic scope 100 is to be inserted (see FIG. 4), and a scope lock lever 12 for locking the inserted connector 104 so as not to come off. The scope socket 11 establishes connection with connect pins, or the like, provided in the connector 104 of the electronic scope 100. A light guide socket 13 for the light guide connector 115 of the electronic scope 100 (or a fiber scope) to be inserted into is formed below the scope socket 11.

The processor 10 also has an operation panel 14 on the front, beside the scope socket 11. This operation panel 14 is provided with operation switches such as a lamp switch 16, an image quality adjustment switch (image quality adjustment button) 17, a light control selection switch (light control selection button) 18, a manual adjustment switch 19, and a scope information display 20. A memory card slot 21 for a removable memory card to be loaded into and a main switch 15 are also formed below the operation panel 14.

The processor 10 contains a rotary aperture plate 50 which is arranged behind the light guide socket 13. This rotary aperture plate 50 has a plurality of aperture openings having different opening ratios, which are arranged in the circumferential direction of this circular plate. An aperture plate drive motor (drive device) 22 rotationally drives so that any one of the aperture openings is opposed to an incident end face 113a of a light guide 113 which is plugged into the light guide socket 13 (see FIG. 4). A condenser lens L is arranged on the opposite side of the rotary aperture plate 50 from the incident end face 113a, with a lamp (light source) 23 provided behind the condenser lens L. As shown in FIG. 5, the light source 23 has a built-in high-intensity lamp 35. Illumination light emitted from the lamp 35 is focused by the condenser lens L so that the light beam passing through any one of the aperture openings of the rotary aperture plate 50 is incident on the incident end face 113a. The vicinity of the incident end face 113a of the light guide 113 is fixed inside a light guide sleeve 114 which is made of metal.

As shown in FIG. 2, the processor 10 also contains a lamp power supply 24 which has an igniter 25 for turning on the light source 23. A cooling fan 26 for cooling the lamp power supply 24 is formed on the rear panel of the processor 10.

In the processor 10, a memory card board 27 is arranged near the memory card slot 21. The memory card board 27 is electrically connected with the memory card loaded in the memory card slot 21, and functions as an interface circuit controls reading and writing from/to the memory card. For example, the read/write control includes reading information written in the memory card, and writing information such as image information processed by the processor 10 to the memory card. The processor 10 also contains a control board 28 on which circuits such as a control circuit (controller/reading device) 41 and an image processing circuit are mounted. The control circuit 41 controls the operations of the entire processor 10, including the control of the memory card board 27 and the aperture plate drive motor 22. The image processing circuit of the control board 28 reads stored information from an EEPROM (memory) 109 of the electronic scope 100, drives a CCD sensor (image pickup device) 105 of the electronic scope 100, processes picture signals obtained by the CCD sensor 105, and displays the processed picture signals on a monitor display 43. The picture signals processed by the control board 28 are output from a picture connector (not shown) provided on a back panel substrate 29. A predetermined picture is then displayed on the monitor display 43.

Figure 3:
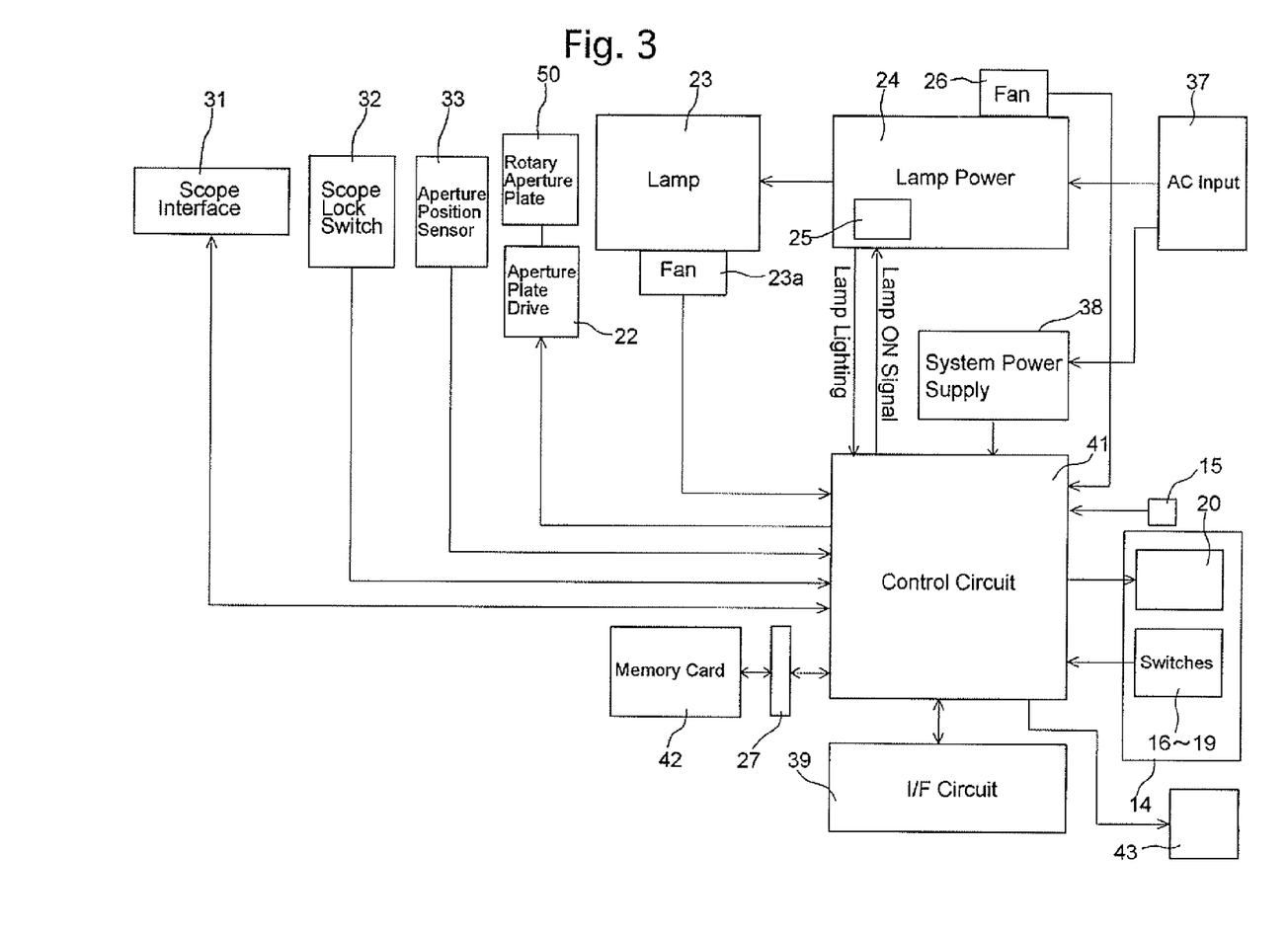
FIG. 3 is a block diagram showing essential circuits of the processor, according to the present invention.

FIG. 3 shows essential components of the circuit configuration of the processor 10. A scope interface 31 is provided inside the scope socket 11. The scope interface 31 is provided with a plurality of connectors, including an information connector and the picture connector. The information connector is for reading information written in the EEPROM 109 of the electronic scope 100. The picture connector transmits a drive clock of the CCD sensor 105, and inputs picture signals output from the CCD sensor 105. Each connector is connected to respective corresponding terminals, such as those of the control circuit 41 formed on the control substrate 28.

A scope lock switch 32 is a detection switch for detecting if the scope lock lever 12 is in a locked state. The state signal of the scope lock switch 32 is input to the control circuit 41.

The aperture plate drive motor 22 for rotationally driving the rotary aperture plate 50 is driven and controlled by the control circuit 41. The rotation position of the rotary aperture plate 50 is detected by an aperture position sensor 33 and the control circuit 41 receives the signal detected thereby.

The light source 23 is turned on by the igniter 25 of the lamp power supply 24 which is controlled ON/OFF by the control circuit 41. The light source 23 is also provided with a lamp cooling fan 23a. The lamp cooling fan 23a is driven and controlled by the control circuit 41. The igniter 25 for turning ON and driving the light source 23 is driven by the lamp power supply 24 which is powered by an AC input 37, typically a commercial alternating-current power.

The AC input 37 also powers a system power supply 38 which outputs a constant voltage for driving electronic circuits such as the control circuit 41. The control circuit 41 is activated to start processing when the main switch 15 is turned ON, and transmits a lamp-ON signal to the lamp power supply 24 to turn ON the light source 23 via the igniter 25 when the lamp switch 16 is turned ON. Furthermore, in the illustrated embodiment, not only can the turning ON of the lamp switch be a condition for turning ON the light source 23, but alternatively the turning ON of the main switch 15 or the turning ON of the scope lock switch 32.

The control circuit 41 also performs image capturing processing for driving the CCD sensor 105 of the electronic scope 100 and inputting an image signal from the CCD sensor via the scope interface 31. Moreover, the control circuit 41 applies a predetermined image signal process, and displays the image signal on a monitor display 43 or writes it to the memory card 42 via the memory card board 27. It should be appreciated that although the control circuit 41 starts the image capturing process when the main switch 15 is turned ON for activation, the image capturing process is usually performed by an image processing circuit which is separate from the control circuit.

The control circuit 41 is also connected with an input device such as a keyboard via an I/F circuit 39 so that individual information necessary for endoscopic inspection can be entered via the input device.

Figure 4:
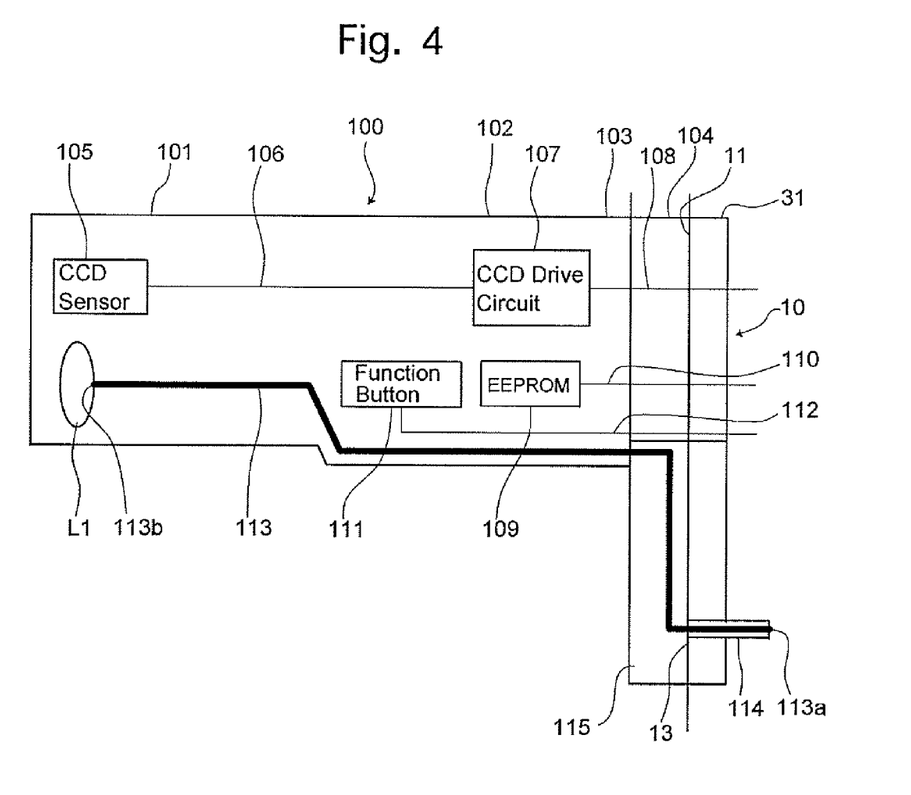
FIG. 4 is a schematic diagram of an electronic scope which is connectable to the processor, according to the present invention.
Figure 5:
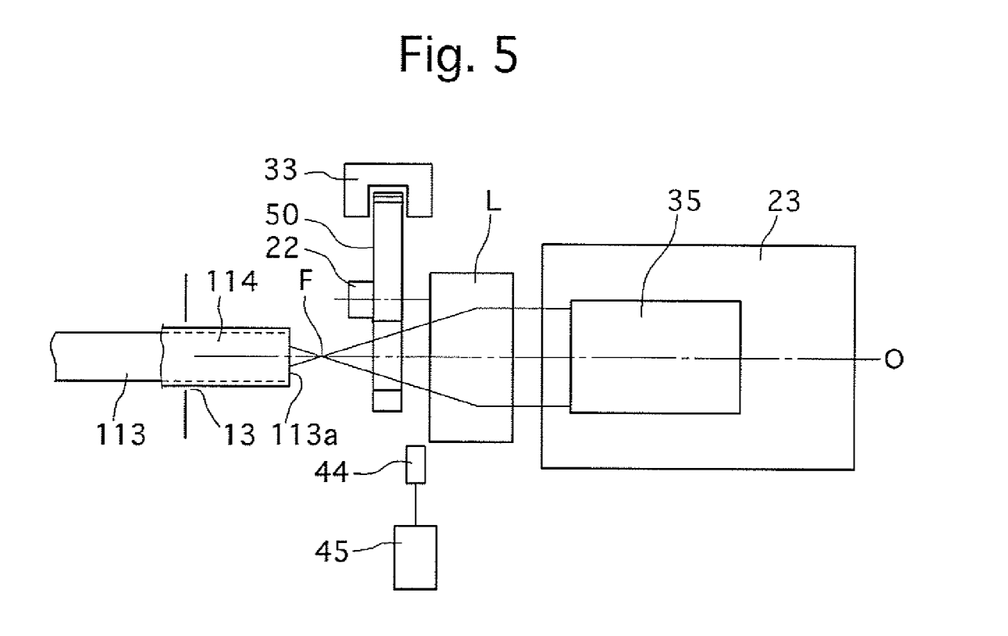
FIG. 5 is an explanatory diagram showing various components which are provided near the light source unit of the processor.

FIG. 4 is a diagram showing a schematic view of the electronic scope 10 which is connected to the processor 10.

As shown in FIG. 4, the electronic scope 100 has a flexible insertion portion 101 and an operation portion 102. The connector 104 is arranged on the top of a universal tube 103 which extends from the operation portion 102. The CCD sensor 105 and a light distribution lens L1 for light illumination are arranged at the distal end of the flexible insertion portion 101. The CCD sensor 105 is connected to a CCD drive circuit 107 formed in the operation portion 102, via a picture line 106 which is laid through the insertion portion 101. The CCD drive circuit 107 is also connected with a picture transmission line that is laid through the operation portion 102 and the universal tube 103. The picture transmission line 108 is connected to signal pins formed in the connector 104. The EEPROM 109, containing such information as the type of the electronic scope 100, is provided in the operation portion 102. A read/write line 110, which is connected with input and output terminals of the EEPROM 109, is connected to signal pins of the connector 104. The operation portion 102 also includes a function button 111 for making operations of taking a moving image, and photographing a still image, etc. A switch line 112 in connection with the contacts of the function button 111 is connected to signal pins in the connector 104. The picture line 108 is connected to the control circuit 41 via the signal pins when the connector 104 is connected to the scope interface 31. Furthermore, the picture signals of an image picked up by the CCD sensor 105 and output there from are input to the control circuit 41.

The exit end 113b of the light guide 113 is placed behind the light distribution lens L1. The light guide 113 is introduced through the insertion portion 101, the operation portion 102, the universal tube 103, and the connector 104, and is inserted and fixed inside the light guide sleeve 114 which protrudes out of the connector 104. The incident end face 113a of the light guide 113 is opposed to the open end of the light guide sleeve 114.

The EEPROM 109 provided in the electronic scope 100 contains at least the information for identifying the type of scope, i.e., an illumination light intensity limit of the scope. In this embodiment, scope types are classified into a plurality of groups stepwise depending on the illumination light intensity limit, i.e., the maximum amounts of light allowed for the light guide 113 to emit. In the present embodiment, the scope types are classified into three groups, i.e., type A, type B, and type C, in descending order of the amount of light.

FIG. 5 is a diagram showing various components which are provided near the light source 23 of the processor 10. As shown in FIG. 5, the rotary aperture plate 50 is interposed between the incident end face 113a of the light guide sleeve 114 (light guide 113), which is inserted from the light guide socket 13, and the condenser lens L which is provided in front of the light source 23. The incident end face 113a is normally placed orthogonal to the optical axis O of the condenser lens L, away from the focal point F of the condenser lens L. The substantially parallel illumination light emitted from the lamp 35 is focused at the focal point F by the condenser lens L, so that the light beam passing through the rotary aperture plate 50 gathers at the focal point F and thereafter diverges so as to be incident on the incident end face 113a. The illumination light beam entering from the incident end face 113a is guided through the light guide 113, and emitted from the exit end 113b (see FIG. 4) of the light guide 113 provided at the distal end of the insertion portion 101. The emitted light then passes through the light distribution lens L1 for distribution (FIG. 4) so as to illuminate an object.

Figure 6:
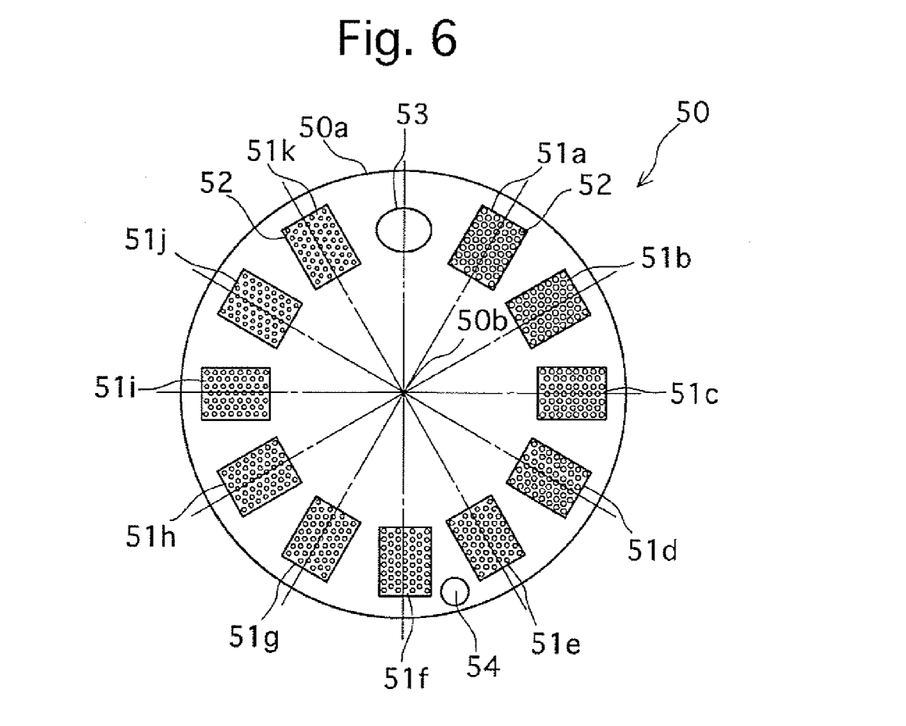
FIG. 6 is a front view of the rotary aperture plate of the aperture device of the light source unit, according to the present invention.

FIG. 6 is a front view of the rotary aperture plate 50 of the aperture device for the light source 23. As shown in FIG. 6, the rotary aperture plate 50 is made of an aluminum disc 50a. The disc 50a is fixed to a rotary shaft of the aperture plate drive motor 22 centered at the center of rotation 50b. The disc 50a has twelve openings which are formed at predetermined intervals circumferentially about the center of rotation 50b (at 30 degree intervals). In the illustrated embodiment, the disc 50a is provided with first to eleventh aperture openings 51a to 51k, and an auxiliary lamp opening 53. The first aperture opening 51a has an opening ratio of 70%. The opening ratios are determined to decrease stepwise, clockwise from the first aperture opening 51a. The second to eleventh aperture openings 51b to 51k have opening ratios of 50%, 35%, 25%, 18%, 13%, 9%, 7%, 5%, 3.5%, and 2%, respectively. The auxiliary lamp opening 53 has an opening ratio of 100%.

In the illustrated embodiment, the first to eleventh aperture openings 51a to 51k have a large number of small holes 52 which are formed at a predetermined spacing in each opening area. The illumination light is either passed through these small holes 52 or blocked by the surface of the disc 50a where the small holes 52 are not formed.

In an embodiment, different opening ratios are achieved by modifying the density (spacing) of the small holes 52 of the first to eleventh aperture openings 51a to 51k. Alternatively, the density (spacing) can be maintained constant and the diameters of the small holes 52 can be modified. Alternatively, both the density (spacing) and the diameter of the small holes 52 can be modified. The small holes 52 can be arranged in either a grid-like configuration or a crossed configuration. The small holes may have any shape. Each aperture opening may be provided with a mixture of small holes of various shapes. The aperture openings may have small holes of respective different shapes. Although circular small holes are easy to form and to modify in diameter, polygonal and other shapes may also be adopted. Polygonal shapes can easily provide higher opening ratios than with circular shapes.

The rotary aperture plate 50 is driven stepwise by the aperture plate drive motor 22. It is desirable for the aperture plate drive motor 22 to be a stepping motor. In the illustrated embodiment, a stepping motor having a step angle of 0.75 degrees is used. Namely, when the aperture plate drive motor 22 rotates by 40 steps, the rotary aperture plate 50 is rotated by 30 degrees, i.e., by one aperture opening.

The rotary aperture plate 50 has an aperture position hole 54 for detecting an initial position of rotation thereof. The aperture position sensor 33 (FIGS. 3 and 5) is arranged so as to detect the aperture position hole 54 when the rotary aperture plate 50 is in the initial position of rotation. The aperture position sensor 33 can be a photo coupler, wherein the aperture position hole 54 opens the optical path of the photo coupler when the rotary aperture plate 50 is in the initial position; the disc 50a otherwise blocks the optical path of the photo coupler. In the present embodiment, the initial position refers to the state where the third aperture opening 51c enters (intersects) the illumination optical path.

As shown in FIG. 5, the processor 10 has an auxiliary light 44 that comes into operation when the lamp 35 of the light source 23 goes out due to some reason. When the control circuit 41 detects that the lamp 35 has gone out, the control circuit 41 activates an auxiliary light drive mechanism 45 to put the auxiliary light 44 into the illumination optical path and turn the auxiliary light ON. The control circuit 41 rotates the rotary aperture plate 50 so that the auxiliary lamp opening 53 enters (intersects) the illumination optical path.

Figure 7:
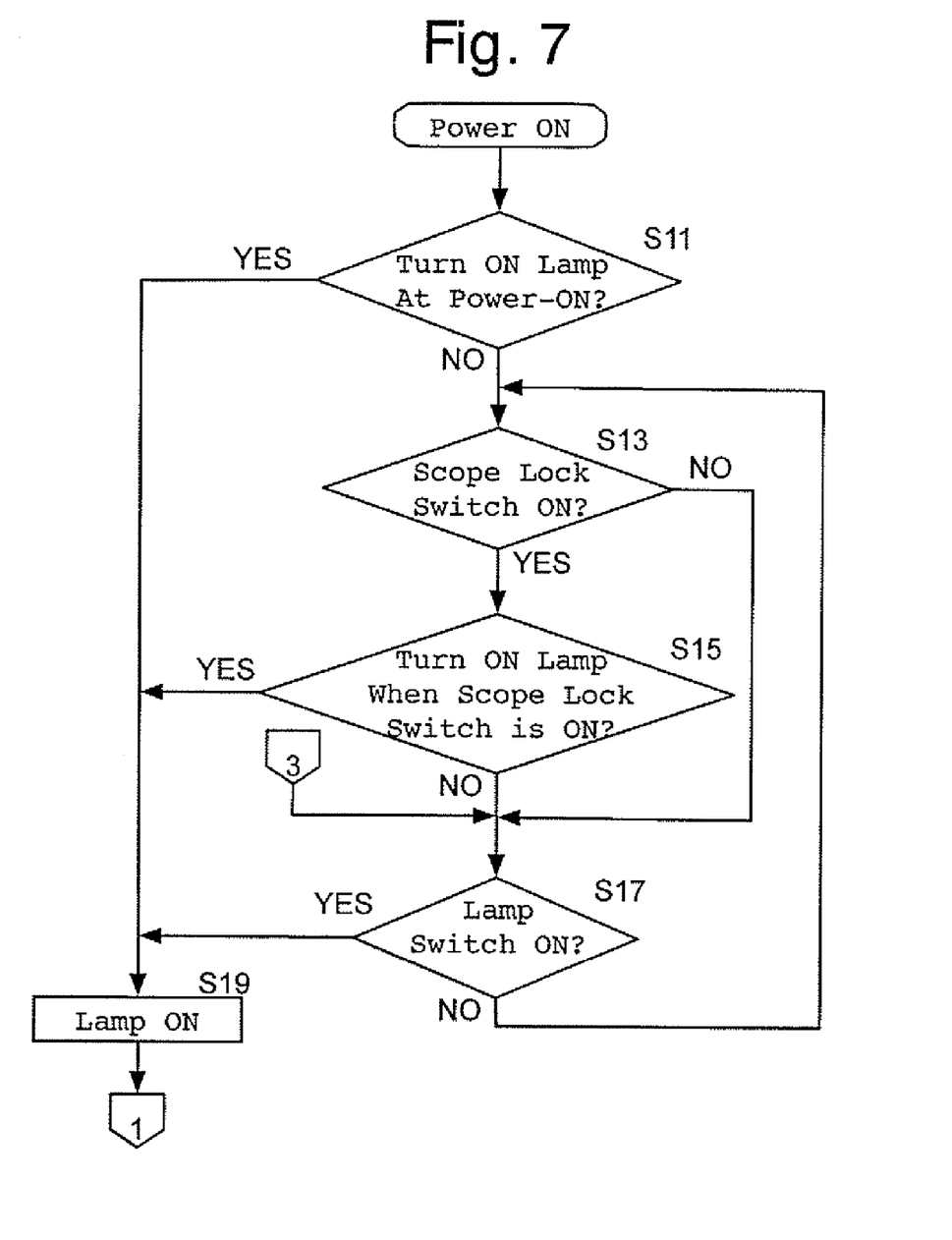
FIG. 7 is a flowchart showing a first half of a control operation for the illumination of the processor.
Figure 8:
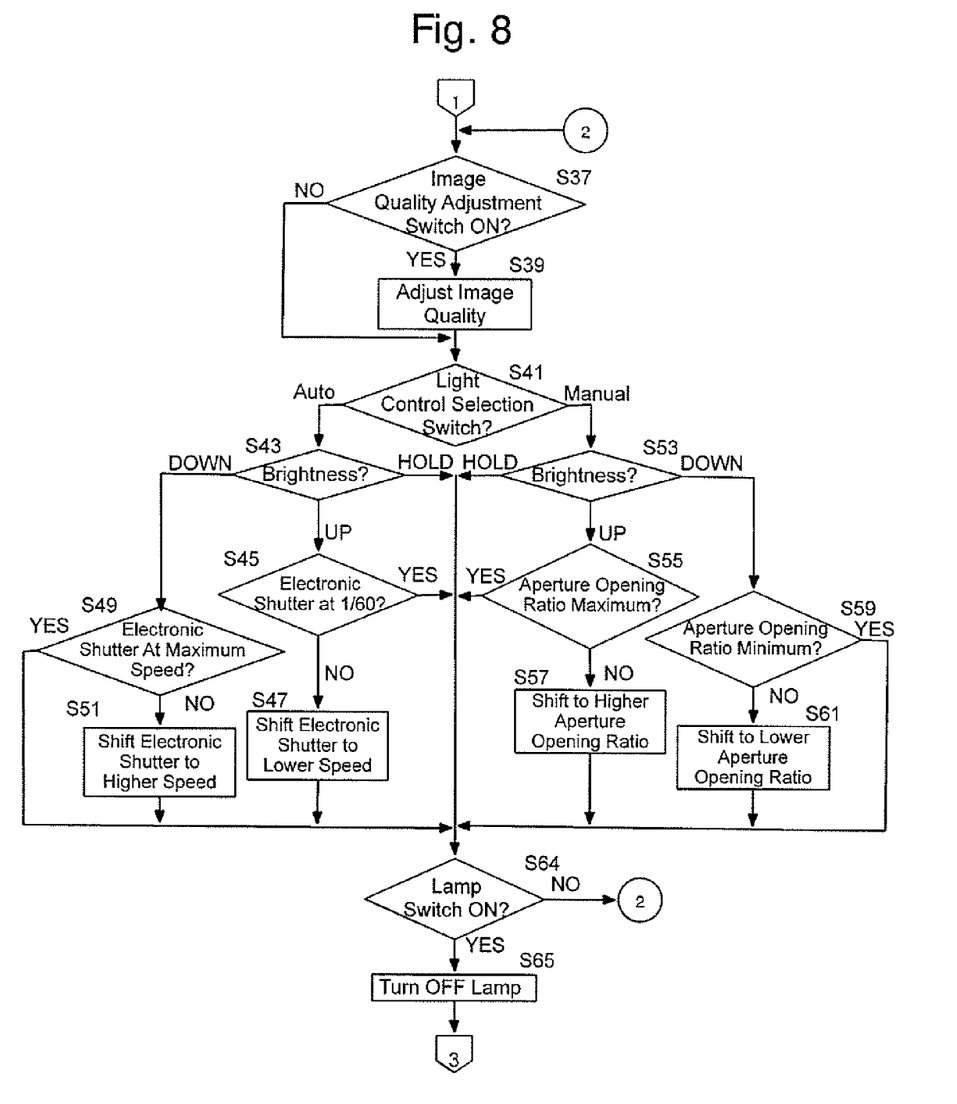
FIG. 8 is a flowchart showing a second half of the control operation for the illumination of the processor.

The operation of the electronic endoscope system will be described with reference to the flowchart of the power-ON process shown in FIGS. 7 and 8. The power-ON process concerns the operation of the control circuit 41. The control circuit 41 enters this power-ON process when the main switch 15 is turned ON. In the illustrated embodiment, either turning ON the main switch 15, turning ON the scope lock switch 32, or turning ON the lamp switch 16 can be selected as the condition (mode) for turning ON the light source 23. Such selection of the condition (mode) for turning ON the light source 23 can be carried out by the I/F circuit 39 via the aforementioned keyboard or can be carried out via a light-ON mode selection switch SWlm provided on the operation panel 14. Note that the initial mode is set to when the lamp switch 16 is turned ON.

Upon entering the power-ON process, the control circuit 41 checks whether or not the timing for a lamp-on process is set to power-ON time (step S11). In other words, the control circuit 41 checks whether or not the mode is selected in which the lamp source 23 is turned ON when the main switch 15 is turned ON. If the lamp-ON timing is set to the power-ON time (step S11, YES), the control circuit 41 turns the lamp ON (step S19), i.e., turns ON the lamp source 23, and control proceeds to step S37 (FIG. 8). If the lamp-ON timing is not set to the power-ON time (step S11, NO), the control circuit 41 proceeds to step S13 without turning on the light source 23.

At step S13, the control circuit 41 checks whether or not the scope lock switch 32 is ON. If the scope lock switch 32 is ON (step S13, YES), the control circuit 41 checks whether or not the lamp-ON timing is set to when the scope lock switch 32 is ON (step S15). Namely, the control circuit 41 checks whether or not the mode is selected in which the lamp source 23 is turned ON when the scope lock switch 32 is ON. If the lamp-ON timing is set to when the scope lock switch 32 is ON (step S15, YES), the control circuit 41 turns ON the light source 23 (step S19), and control proceeds to step S37. It the lamp-ON timing is not set to when the scope lock switch 32 is ON (step S15, NO), the control circuit 41 proceeds to step S17 without turning on the lamp source 23. If the scope lock switch 32 is not ON (step S13, NO), control proceeds to step S17.

At step S17, the control circuit 41 checks whether or not the lamp switch 16 is operated while the lamp source 23 is OFF. If the lamp switch 16 is operated (step S17; YES), the control circuit 41 turns ON the light source 23 (step S19), and control proceeds to step S37. If the lamp switch 16 is not operated (step S17, NO), control returns to step S13. It should be noted that the lamp switch 16 of the illustrated embodiment is a momentary switch. The control circuit 41 turns ON the lamp 35 if the lamp switch 16 is operated when the lamp 35 is OFF, and turns OFF the lamp 35 if the lamp switch 16 is operated when the lamp 35 is ON.

At step S37, the control circuit 41 checks whether or not the image quality adjustment switch 17 is ON. If the image quality adjustment switch 17 is ON, the control circuit 41 makes an image quality adjustment and proceeds to step S41 (step S37, YES; S39, S41). If the image adjustment switch 17 is not ON, the control circuit 41 skips the image quality adjustment and proceeds to step S41 (step S37, NO; S41).

At step S41, the control circuit 41 checks whether automatic light control or manual light control has selected by the light control selection switch 18.

If the automatic light control is selected (step S41, AUTO), the control circuit 41 checks whether to increase, decrease, or hold the brightness based on the brightness of the object image measured by the control circuit 41 (step S43). In order to increase the brightness (step S43, UP), i.e., adjust toward an overexposure, the control circuit 41 checks whether or not the electronic shutter is set to a minimum speed of 1/60 seconds (step S45). If the shutter speed is already set to 1/60 seconds, the control circuit 41 simply proceeds to step S63 since it is impossible to slow down the shutter speed further (step S45; YES, S63). If the shutter speed is not set to 1/60 seconds (step S45, NO), the control circuit 41 shifts the electronic shutter to a slower speed (step S47), and proceeds to step S63.

In order to decrease the brightness (step S43, DOWN), i.e., adjust toward an underexposure, the control circuit 41 checks whether or not the electronic shutter is set to a maximum speed (step S49). If the electronic shutter is set to the maximum speed (step S49. YES), the control circuit 41 simply proceeds to step S63. If the electronic shutter is not set to the maximum speed (step S49, NO), the control circuit 41 shifts the electronic shutter to a higher speed (step S51), and proceeds to step S63.

To hold the brightness (step S43; HOLD), i.e., make no adjustment on the exposure, the control circuit 41 simply proceeds to step S63.

If the manual light control is selected (step S41, MANUAL), the control circuit 41 checks whether brightness UP, DOWN, or HOLD has selected by the manual adjustment switch 19 (step S53). It should be noted that when the manual light control is selected in the illustrated embodiment, the electronic shutter speed is fixed to 1/60 seconds.

If brightness UP is selected by the manual adjustment switch 19 (step S53, UP), the control circuit 41 checks whether or not the aperture opening ratio is set to a maximum value. If the aperture opening ratio is set to the maximum value (step S55, YES), the control circuit 41 simply proceeds to step S63. If the aperture opening ratio is not set to the maximum value (step S55, NO), the control circuit 41 shifts (rotates) the rotary aperture plate 50 to a higher aperture opening ratio, up to the next level (step S57), and proceeds to step S63.

If brightness DOWN is selected by the manual adjustment switch 19 (step S53, DOWN), the control circuit 41 checks whether or not the aperture opening ratio is set to a minimum value (step S59). If the aperture opening ratio is set to the minimum value (step S59, YES), the control circuit 41 simply proceeds to step S63. If the aperture opening ratio is not set to the minimum value (step S59, NO), the control circuit 41 shifts the aperture opening ratio, namely, rotates the rotary aperture plate 50 down to the next level (step S61), and proceeds to step S63.

If no selection is made by the manual adjustment switch 19 (step S53, HOLD), the control circuit 41 simply proceeds to step S63.

At step S63, the control circuit 41 checks whether or not the lamp switch 16 is operated while the lamp 35 is ON. If the lamp switch 16 is not operated (step S63, NO), the control circuit 41 returns to step S37. If the lamp switch 16 is operated (step S63, YES), the control circuit 41 turns OFF the lamp 35 (step S65), and returns to step S33.

When the main switch 15 is turned OFF, the control circuit 41 turns OFF the light source 23 and exits via an interrupt process.

According to the above description, other than when the lamp switch 16 is turned ON, the timing for turning ON the lamp source 23 can be selected from either when the main switch 15 is turned ON or when the scope lock switch 32 is turned ON. It is therefore possible to turn ON the lamp source 23 without performing a separate ON operation for the lamp switch 16.

Moreover, according to the illustrated embodiment of the present invention, the ON operation of the lamp switch 16 constitutes a condition for turning OFF the lamp source 23 that is turned ON. It is therefore possible to turn OFF the lamp source 23 by making the ON operation of the lamp switch 16 independent of the lamp-ON condition. Subsequently, the lamp switch 16 can be operated to turn ON the lamp source 23 again regardless of the lamp-ON condition. Moreover, if the lamp-ON condition is ON for the scope lock switch 32, the lamp source 23 can also be turned ON by turning ON the scope lock switch 32.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An electronic endoscope apparatus comprising:
   an endoscope light source unit for making illumination light from a light source incident on an incident end face of a light guide of a scope which is detachably connected to a processor, the endoscope light source unit being built in said processor;
   a main switch for turning ON said processor;
   a scope lock lever for activating a lock mechanism for preventing said connected scope from coming off said processor;
   a light source switch for turning ON and OFF said endoscope light source unit; and
   a controller for turning ON said endoscope light source unit when said scope lock lever is operated in a locked state before said light source switch is operated while the endoscope light source unit is OFF.

2. The electronic endoscope apparatus according to claim 1, wherein said processor comprises a scope lock switch for detecting whether said scope lock lever is in a locked state; where said controller turns ON said endoscope light source unit when said scope lock switch detects said locked state.

3. The electronic endoscope apparatus according to claim 2, wherein said controller selects one of said main switch, said scope lock switch, and said light source switch as a condition for turning ON said endoscope light source unit, so that said controller turns ON said endoscope light source unit when said one of said main switch, said scope lock switch, and said light source switch is turned ON.

4. The electronic endoscope apparatus according to claim 2, wherein said controller selects said main switch as a condition for turning ON said endoscope light source unit, so that said controller turns ON said endoscope light when said main switch is turned ON.

5. The electronic endoscope apparatus according to claim 2, wherein said controller selects said scope lock switch as a condition for turning ON said endoscope light source unit, so that said controller turns ON said endoscope light when said scope lock switch is operated in a locked state.

6. The electronic endoscope apparatus according to claim 5, wherein while said scope lock switch is not in said locked state, said controller turns ON said endoscope light when said light source switch is turned ON.

7. The electronic endoscope apparatus according to claim 1, wherein said controller turns OFF said endoscope light source unit when one of said main switch and said light source switch is turned OFF.

* * * * *